(12) United States Patent
Flannery

(10) Patent No.: US 11,953,192 B1
(45) Date of Patent: Apr. 9, 2024

(54) FOGGING MACHINE VISUAL AID AND TUNING DEVICE

(71) Applicant: Brian Flannery, East Hampton, CT (US)

(72) Inventor: Brian Flannery, East Hampton, CT (US)

(*) Notice: Subject to any disclaimer, the term of this patent is extended or adjusted under 35 U.S.C. 154(b) by 0 days.

(21) Appl. No.: 18/501,054

(22) Filed: Nov. 3, 2023

Related U.S. Application Data

(60) Provisional application No. 63/502,715, filed on May 17, 2023.

(51) Int. Cl.
| | | |
|---|---|---|
| *F21V 33/00* | (2006.01) | |
| *A61L 2/18* | (2006.01) | |
| *A62C 33/00* | (2006.01) | |
| *B05B 7/00* | (2006.01) | |
| *B05B 12/00* | (2018.01) | |
| *B05B 12/16* | (2018.01) | |
| *B05B 15/652* | (2018.01) | |
| *F21V 21/088* | (2006.01) | |
| *F21S 10/00* | (2006.01) | |

(52) U.S. Cl.
CPC ............ *F21V 33/00* (2013.01); *A61L 2/18* (2013.01); *A62C 33/00* (2013.01); *B05B 7/0075* (2013.01); *B05B 12/002* (2013.01); *B05B 12/16* (2018.02); *B05B 15/652* (2018.02); *F21V 21/0885* (2013.01); *F21S 10/002* (2013.01); *F21V 33/0064* (2013.01)

(58) Field of Classification Search
CPC . F21V 33/0064; F21V 21/0885; A62C 33/00; F21S 10/002
See application file for complete search history.

(56) References Cited

U.S. PATENT DOCUMENTS

| | | | | |
|---|---|---|---|---|
| 1,268,622 A | * | 6/1918 | Reynolds | F21V 21/08 362/396 |
| 2,041,332 A | * | 5/1936 | Golden | F21V 21/0885 248/305 |
| 2,042,385 A | * | 5/1936 | Boring | B65D 90/00 362/396 |
| 2,105,632 A | * | 1/1938 | Bernesser | B67D 7/425 362/96 |
| 2,637,062 A | | 5/1953 | Sutton et al. | |
| 4,932,592 A | * | 6/1990 | Abbott | B05B 15/62 239/587.5 |
| 6,951,409 B2 | * | 10/2005 | Hsien | B25B 23/18 362/398 |

(Continued)

*Primary Examiner* — Alexander K Garlen
(74) *Attorney, Agent, or Firm* — Emanus, LLC; Willie Jacques

(57) ABSTRACT

A device is disclosed that may include a housing configured to snap onto a wand of a fogging machine near the nozzle. In addition, the device may include a positioning ramp fixedly attached to the housing. The device may include a cradle configured to hold a flashlight fixedly attached to the positioning ramp. Moreover, the device may include where the positioning ramp is configured to aim the beam of the flashlight obliquely at the nozzle to illuminate the spray pattern of the air liquid mixture exiting the nozzle. Also, the device is further configured to allow real-time adjustment of the spray pattern and droplet size of the air liquid mixture. Further, the device may include the apparatus being removably attached to the wand such that it may be utilized on various wands.

9 Claims, 3 Drawing Sheets

(56) References Cited

U.S. PATENT DOCUMENTS

| | | | |
|---|---|---|---|
| 7,404,649 B2 * | 7/2008 | Gosis | F21V 33/004 362/101 |
| 9,021,737 B1 * | 5/2015 | Bradstreet | A01K 87/00 43/25 |
| 11,167,300 B1 | 11/2021 | Leifeste et al. | |
| 2002/0105794 A1 * | 8/2002 | Hanscom | F21V 33/0084 362/602 |
| 2002/0105797 A1 * | 8/2002 | Navid | F21V 33/0084 362/120 |
| 2005/0024872 A1 * | 2/2005 | Love | F21V 33/008 362/253 |
| 2005/0036300 A1 | 2/2005 | Dowling et al. | |
| 2008/0301903 A1 * | 12/2008 | Cunningham | A47L 9/30 15/410 |
| 2010/0188863 A1 * | 7/2010 | West | F21V 21/0885 362/418 |
| 2013/0098478 A1 * | 4/2013 | Kling | A62C 33/00 137/551 |
| 2017/0089555 A1 * | 3/2017 | Honeycutt, III | F21L 4/027 |
| 2018/0274778 A1 * | 9/2018 | Fulkerson | F21V 23/003 |
| 2020/0229671 A1 * | 7/2020 | Cullins | A46B 15/0055 |
| 2021/0069736 A1 | 3/2021 | Wright | |
| 2021/0386050 A1 * | 12/2021 | Garmendia Oyarbide | A01M 7/0089 |
| 2022/0168455 A1 | 6/2022 | Hirsch et al. | |
| 2022/0369614 A1 | 11/2022 | White | |
| 2022/0371034 A1 | 11/2022 | Oswald et al. | |

* cited by examiner

FOGGING MACHINE VISUAL AID AND TUNING DEVICE

FIELD OF THE INVENTION

This application is a non-provisional patent application claims the priority benefit from the provisional patent application having application No. 63/502,715 filed on May 17, 2023, which is incorporated herein by reference for all purpose in its entirety.

FIELD OF THE INVENTION

The present invention relates generally to a fogging machines and, more particularly, to an illuminator attachment for a fogging machine that illuminates the spray pattern of liquid exiting the nozzle and allows real-time adjustment of the spray pattern.

BACKGROUND OF THE INVENTION

Fogging machines are commonly used in a variety of settings, including agriculture, pest control, and sanitation. The fogging machines generate a mist or fog that is composed of small droplets of liquid, which can be used to apply chemicals, disinfectants, or other substances to a surface or area. The fogging machines typically include a wand or spray nozzle that dispenses the mist or fog.

One of the challenges associated with using the fogging machine is that it can be difficult to see the spray pattern of liquid exiting the nozzle. This can make it difficult to adjust and tune the device ensure that the liquid is being applied evenly and effectively. Additionally, the fogging machines are often used in dark areas, such as crawl spaces or basements, which can further exacerbate the visibility issue.

There have been some attempts to address this problem by attaching lights to fogging machines. However, these solutions have been inadequate because they do not effectively illuminate the spray pattern of liquid exiting the nozzle. For example, some prior art solutions simply attach a flashlight to the wand or the body of the fogging machine, which can cast shadows and create glare, making it difficult to see the spray pattern.

Therefore, there is a need for an improved illuminator attachment for fogging machines that effectively illuminates the spray pattern of liquid exiting the nozzle and allows real-time adjustment of the spray pattern.

SUMMARY OF THE INVENTION

The present invention is an illuminator attachment designed to attach to the wand of a fogging machine near the end of the spray nozzle. The illuminator attachment snaps onto the wand and the flashlight snaps into a cradle on the attachment. The attachment includes a positioning ramp configured to aim the beam of the flashlight obliquely at the nozzle to illuminate the spray pattern of liquid exiting the nozzle. The spray pattern reflects the light toward the user and allows real-time adjustment of the spray pattern. The flashlight further allows the use of the fogging machine in dark areas. The illuminator attachment is removably attached to the wand such that it may be utilized on various wands and is not a permanent feature of the wand.

DETAILED DESCRIPTION OF THE INVENTION

The present invention is an illuminator and an illuminator attachment for fogging and spraying machines that effectively illuminates the spray pattern of liquid droplets exiting the nozzle of the fogging machine and allows real-time adjustment of the spray pattern. The illuminator attachment is designed to attach to the wand of a fogging machinenear the spray nozzle.

Figure 1:
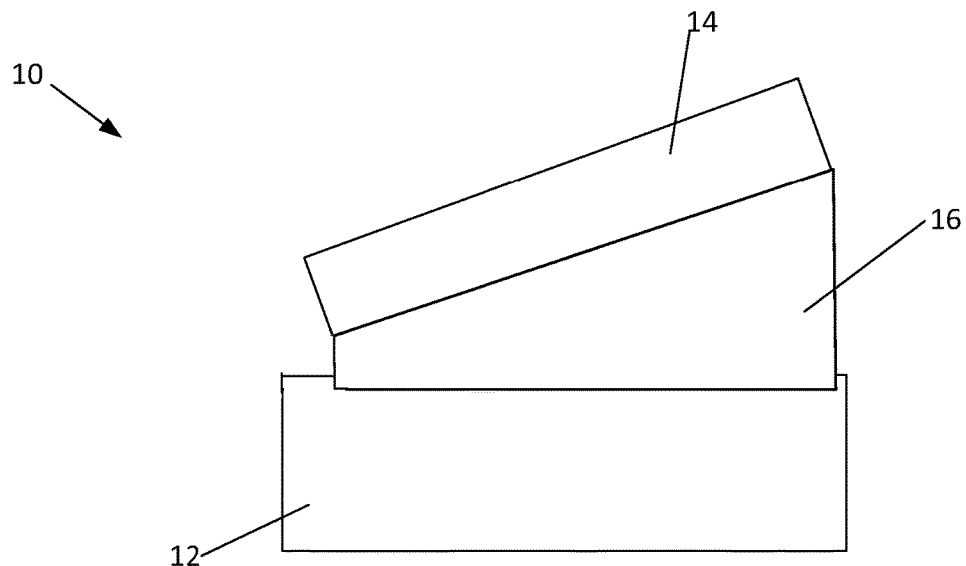
FIG. 1 is a right side view of an illuminator attachment for fogging machines in accordance with the current disclosure.

FIG. 1 is a right side view of an illuminator attachment 10 for fogging machines. The illuminator attachment 10 includes a housing 12, a cradle 14, and a positioning ramp 16. As will be disclosed in more detail herein after, the housing 12 is configured to snap onto a wand of a fogging machine (not shown). The cradle 14 is configured to hold an illuminator, such as a flashlight (FIGS. 4, 5) and snaps onto the housing 12. The positioning ramp 16 configured to aim a beam of the flashlight obliquely at a nozzle to illuminate a spray pattern of liquid exiting the nozzle.

Figure 2:
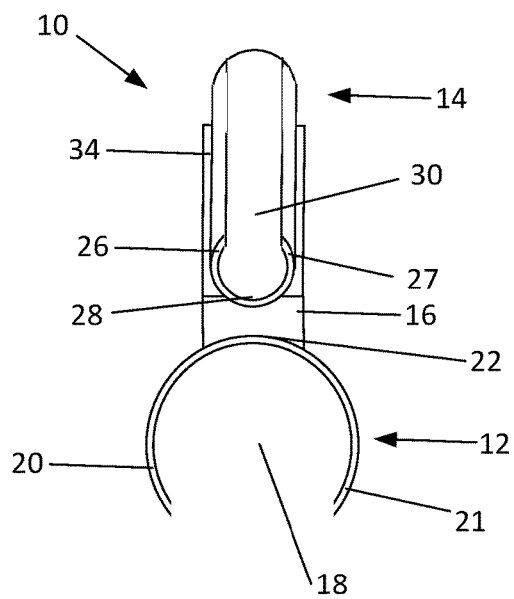
FIG. 2 is a rear view of the illuminator attachment in accordance with the current disclosure.
Figure 3:
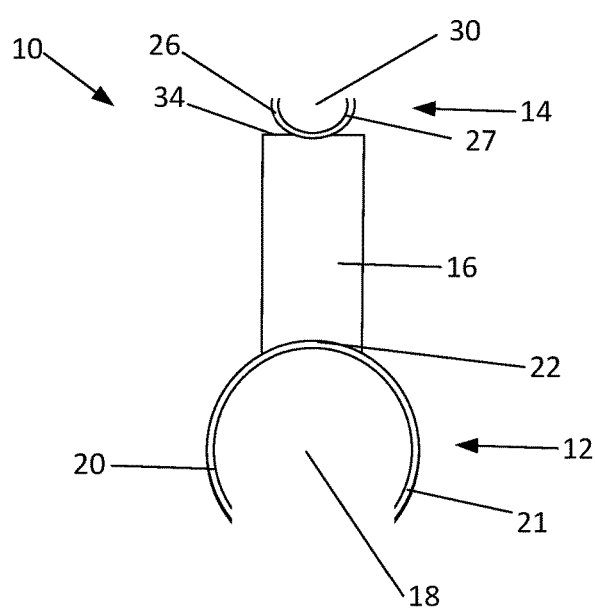
FIG. 3 is a front view of the illuminator attachment in accordance with the current disclosure.

FIG. 2 is a rear view of illuminator attachment 10 and FIG. 3 is a front view of the illuminator attachment 10. As shown in the figures, the housing 12 includes a channel 18 that is sized and shaped to receive the wand of the fogging machine. The channel 18 includes a pair of opposed walls 20, 21 that engage the wand when the housing 12 is snapped onto the wand as will be disclosed in more detail herein after. The walls 20, 21 are resilient, allowing the housing 12 to securely grip the wand.

In some embodiments, the cradle 14 includes a pair of opposed sidewalls 26, 27 and a bottom wall 28 that define a cavity 30 sized and shaped to receive the flashlight. The opposed sidewalls 26, 27 and bottom wall 28 are resilient, allowing the cradle 14 to securely hold the flashlight.

In some embodiments, the positioning ramp 16 includes a recess 22 that is sized and shaped to fit the outside of the housing 12. The positioning ramp 16 may be integrally formed with the housing 12 and extends upwardly from the recess 22. Further, the positioning ramp 16 includes a ramp surface 34 that is angled with respect to the channel 18. As will be appreciated by those skilled in the art and will be disclosed in more detail herein after, the ramp surface 34 is configured to reflect the beam of the flashlight obliquely at the nozzle to illuminate the spray pattern of liquid exiting the nozzle. The ramp surface 34 is shown as providing a fixed angle between the housing 12 and the cradle 14 but adjustable embodiments of the ramp 16 are contemplated by the present disclosure.

Figure 4:
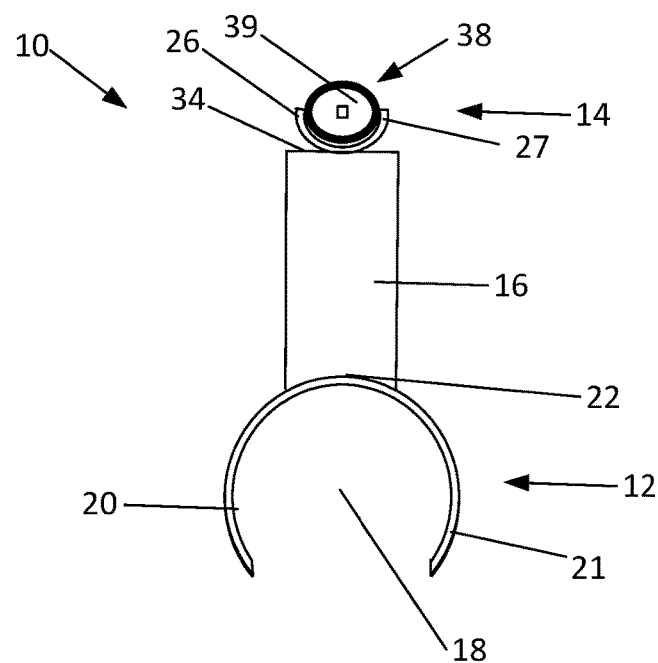
FIG. 4 is a front view of the illuminator attachment with a light installed in accordance with the current disclosure.

FIG. 4 is a front view of the illuminator attachment 10 including an illuminator in the form of a flashlight 38 removably positioned within the cavity 30 (FIGS. 2, 3) and is held in place by the opposed sidewalls 26, 27.

Figure 5:
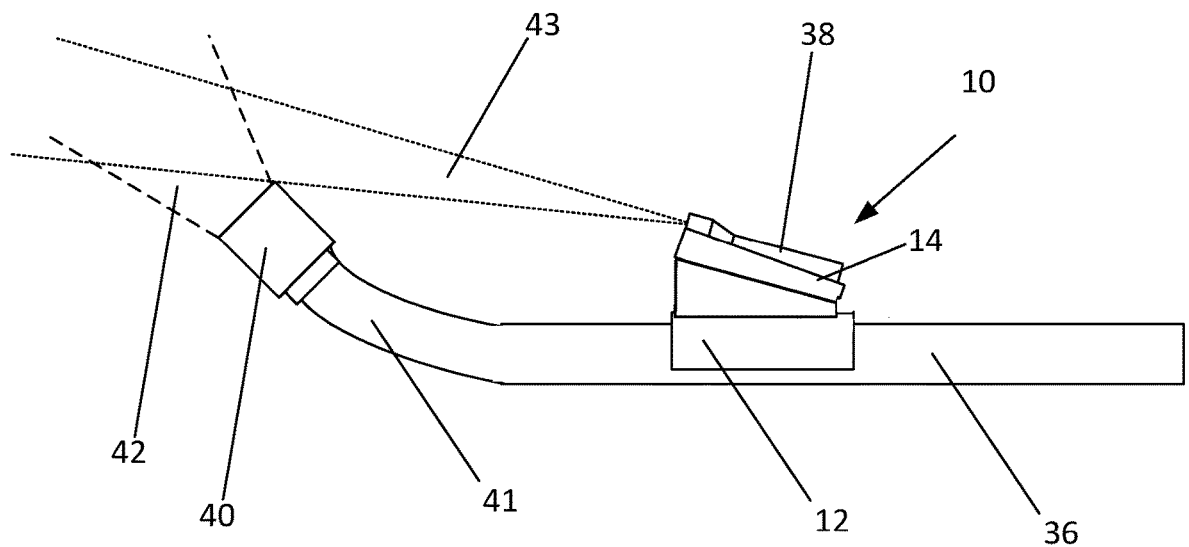
FIG. 5 is a left side view of a wand of a fogging machine with the illuminator attachment installed in accordance with the current disclosure.

Now with reference to FIG. 5, there is shown a left side view of the illuminator attachment 10 removably attached to a wand 36 of a fogging machine (not shown). As shown in the figure, the housing 12 is snapped onto the wand 36 of the fogging machine. The cradle 14 is snapped onto the housing 12 and a flashlight 38 is held in the cavity 30 of the cradle 14. Further, the wand 36 includes a curved portion 41 and a nozzle 40 positioned at the end of the wand 36. It should be appreciated by those skilled in the art that liquid exits the nozzle 40 in a spray form wherein the quality of the spray 42 may be adjusted to provide a predetermined pattern. The spray 42 may be adjusted by adjusting parameters of the fogging machine (pressure, volume, mixture, etc.) or by adjusting the nozzle 40. As may be seen in the figure FIG. 5, the beam 43 of the flashlight 38 is directed obliquely at the spray 42 exiting the nozzle 40 that is further illuminating the spray pattern 42 of the liquid droplets exiting the nozzle 40. The illuminated spray pattern 42 reflects the light from beam 43 back toward the user and allows real-time adjustment of the spray pattern.

The illuminator attachment 10 is removably attached to the wand 36 such that it may be utilized on various wands and in some embodiments of the current disclosure is not a permanent feature of the wand. This allows the illuminator attachment 10 to be easily moved from one fogging machine to another, or from one wand to another, without the need for any special tools or equipment.

The illuminator attachment 10 is particularly useful in dark areas where visibility is limited. For example, the illuminator attachment 10 may be used to apply chemicals, disinfectants, or other substances in crawl spaces, basements, or other areas that are not well lit. The illuminator attachment 10 may also be used during nighttime applications or in areas that are temporarily without power.

In addition to its usefulness in illuminating the spray pattern 12 of liquid exiting the nozzle 40, the illuminator attachment 10 is also easy to use and install. The housing 12 and cradle 14 are designed to snap onto the wand 36 and snap into the flashlight respectively, allowing for quick and easy installation and removal. The positioning ramp 16 is fixedly attached to the housing 12, eliminating the need for any additional attachments or tools.

Figure 6:
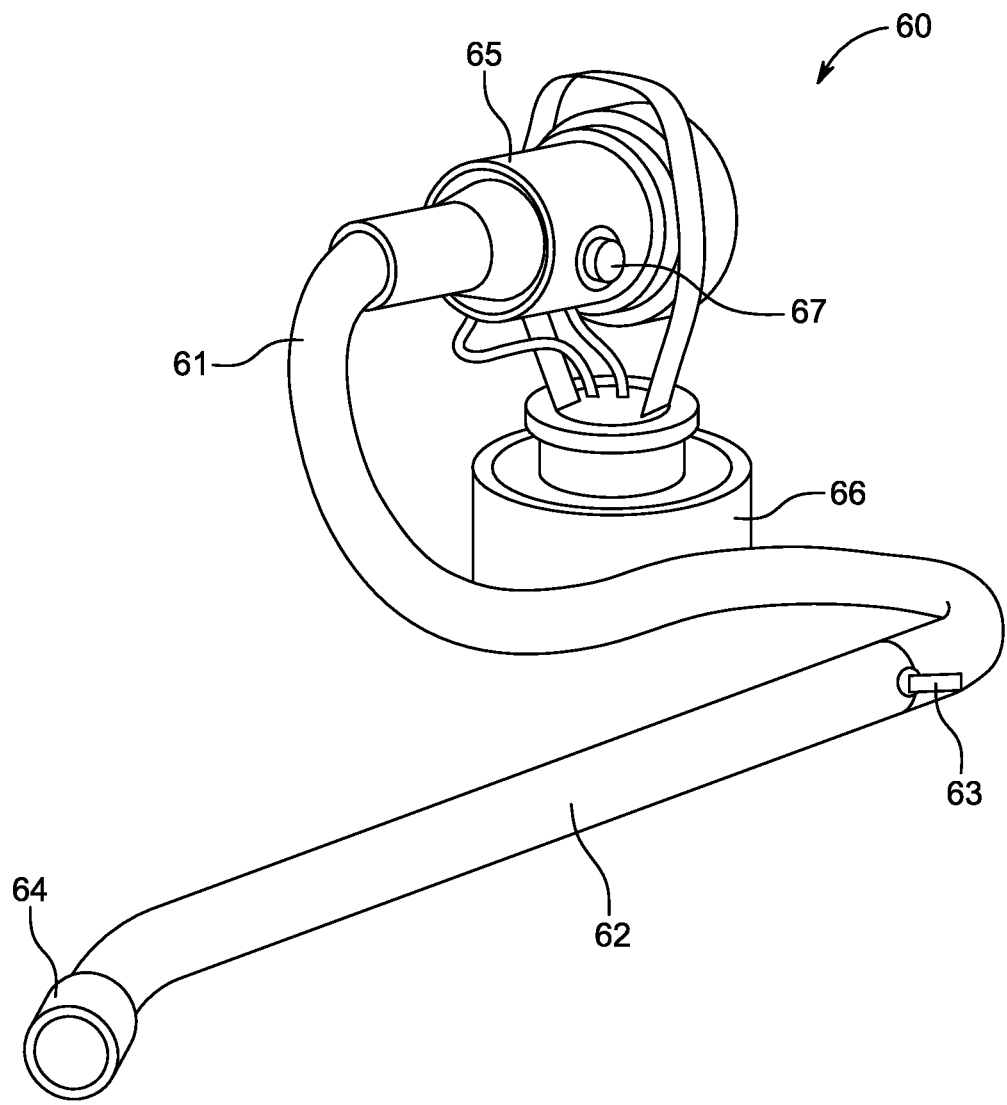
FIG. 6 is a perspective view of a fogging machine of the prior art.

An exemplary fogging machine is a Noz-L-Jet 7807 fogger manufactured by Fogmaster and is shown in FIG. 6 as a fogger 60. The fogger 60 includes a hose 61 and wand E with a discharge control lever 63 mounted on a wand 62 and a nozzle 64 mounted on a distal end of the wand 62. The fogger 60 further includes a power head 65 positioned in fluid communication with a tank 66 and the hose 61. The tank 66 is configured to store and supply a liquid of choice, such as a cleaner, a germicide, anti-mildew chemicals and the like. Further, the fogger 60 includes a motor driven fan (not shown) in the power head 65 to propel an air liquid mixture through hose 62 and out the nozzle 64. The power head 65 further includes a control valve 67 which allows a user to adjust the liquid flow rate and the droplet size of the liquid discharged out of the nozzle 64. In this particular example, the droplet size is adjustable between 10 and 30 microns although liquid viscosity and surface tension affect droplet size. The liquid flow rate controls fog characteristics and average droplet size. A low rate (1-2 ounces [30-60 ml] per minute) produces a dry fog of small droplets that float extensively and diffuse widely. Larger flow rates (4-8 ounces [100-250 ml] per minute) produce progressively larger droplets (wet fog, fine mist). With reference back to FIG. 5, with the illuminator attachment 10 positioned on the wand 62 a user may calibrate the droplet size. The user switches the flashlight 38 on to produce the beam 43 and operates the fogger 60 by pressing the discharge control lever 63 to produce the spray pattern 42. With the spray pattern 42 illuminated by the beam 43 the user may visually calibrate the droplet size by adjusting the control valve 67. Opening the control valve 67 produces large droplets which settle quickly and closing the valve more produces smaller fog droplets with longer float times which may aid in better penetration of a substrate of interest.

The illuminator attachment 10 allows the user, among other things, to apply germicides to air-conditioning ducts, directed fog applications including removing smoke odors from draperies and upholstery, to apply anti-mildew chemicals beneath carpets, and pest control in restaurants and commercial kitchens (treating wall voids, above ceilings and under appliances).

While the invention has been described with reference to specific embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiments disclosed as the best mode contemplated for carrying out this invention, but that the invention will include all embodiments falling within the scope of the appended claims.

In summary, the present invention provides an improved illuminator attachment for fogging machines that effectively illuminates the spray pattern and droplet size of liquid-air mixture exiting the nozzle and allows real-time adjustment of the spray pattern and droplet size. The illuminator attachment is easy to install and use and is removably attached to the wand, allowing for versatility and flexibility in its use. The illuminator attachment is particularly useful in dark areas where visibility is limited and can be used to apply chemicals, disinfectants, or other substances in a variety of settings.

What is claimed is:

1. An apparatus for illuminating a spray pattern of a liquid air mixture exiting a fogging machine nozzle, comprising:
   a housing configured to snap onto a wand of the fogging machine near the nozzle;
   a positioning ramp fixedly attached to the housing; and
   a cradle configured to hold a flashlight fixedly attached to the positioning ramp;
   wherein the positioning ramp includes a ramp surface that is angled away from the housing and the wand in a direction towards the nozzle when snapped onto the wand and is configured to aim the beam of the flashlight obliquely at the nozzle to illuminate the spray pattern of the liquid air mixture exiting the nozzle.

2. The apparatus of claim 1, wherein the housing includes a channel sized and shaped to receive the wand of the fogging machine.

3. The apparatus of claim 2, wherein the channel includes a pair of opposed walls that engage the wand.

4. The apparatus of claim 1, wherein the cradle includes a pair of opposed sidewalls and a bottom wall that define a cavity sized and shaped to receive the flashlight.

5. The apparatus of claim 4, wherein the sidewalls and bottom wall are resilient, allowing the cradle to securely hold the flashlight.

6. The apparatus of claim 1, wherein the apparatus is used to apply chemicals, disinfectants, or other substances to a surface or area.

7. The apparatus of claim 1, wherein the apparatus is further configured to allow real-time adjustment of the spray pattern.

8. The apparatus of claim 1, wherein the apparatus is further configured to allow real-time adjustment of a droplet size of the liquid air mixture.

9. The apparatus of claim 1, wherein the apparatus is configured to be removably attached to the wand such that it may be utilized on various wands.

\* \* \* \* \*